United States Patent [19]
Nixon

[11] 4,023,575
[45] May 17, 1977

[54] CONTOUR BUSTETTE
[76] Inventor: Letha R. Nixon, P.O. Box 315, Denver City, Tex. 79323
[22] Filed: Mar. 2, 1976
[21] Appl. No.: 663,045
[52] U.S. Cl. .................................. 128/481; 3/36
[51] Int. Cl.² ........................................ A41C 3/10
[58] Field of Search .......... 128/478, 481, 479, 480, 128/482, 460

[56] References Cited
UNITED STATES PATENTS

| | | | |
|---|---|---|---|
| 2,867,818 | 1/1959 | Creamer | 3/36 |
| 3,046,990 | 7/1962 | Dozier | 128/460 |
| 3,619,819 | 11/1971 | Mann | 128/481 |
| 3,641,592 | 2/1972 | Den Bleyker | 3/36 |
| 3,896,506 | 7/1975 | Hankin et al. | 3/36 |

Primary Examiner—Werner H. Schroeder
Assistant Examiner—Doris L. Troutman
Attorney, Agent, or Firm—Clarence A. O'Brien; Harvey B. Jacobson

[57] ABSTRACT

A prosthesis to replace a surgically removed breast has a single panel in contact with the body of the wearer within the cup and underarm portion of a conventional brassiere. The brassiere-contacting surface of the prosthesis is formed by upper and lower front panels interconnected along a seam aligned with the horizontal seam of the brassiere. The centerline of the brassiere is aligned with a releasable closure retaining a filler between the front and rear panels.

5 Claims, 5 Drawing Figures

U.S. Patent  May 17, 1977  4,023,575
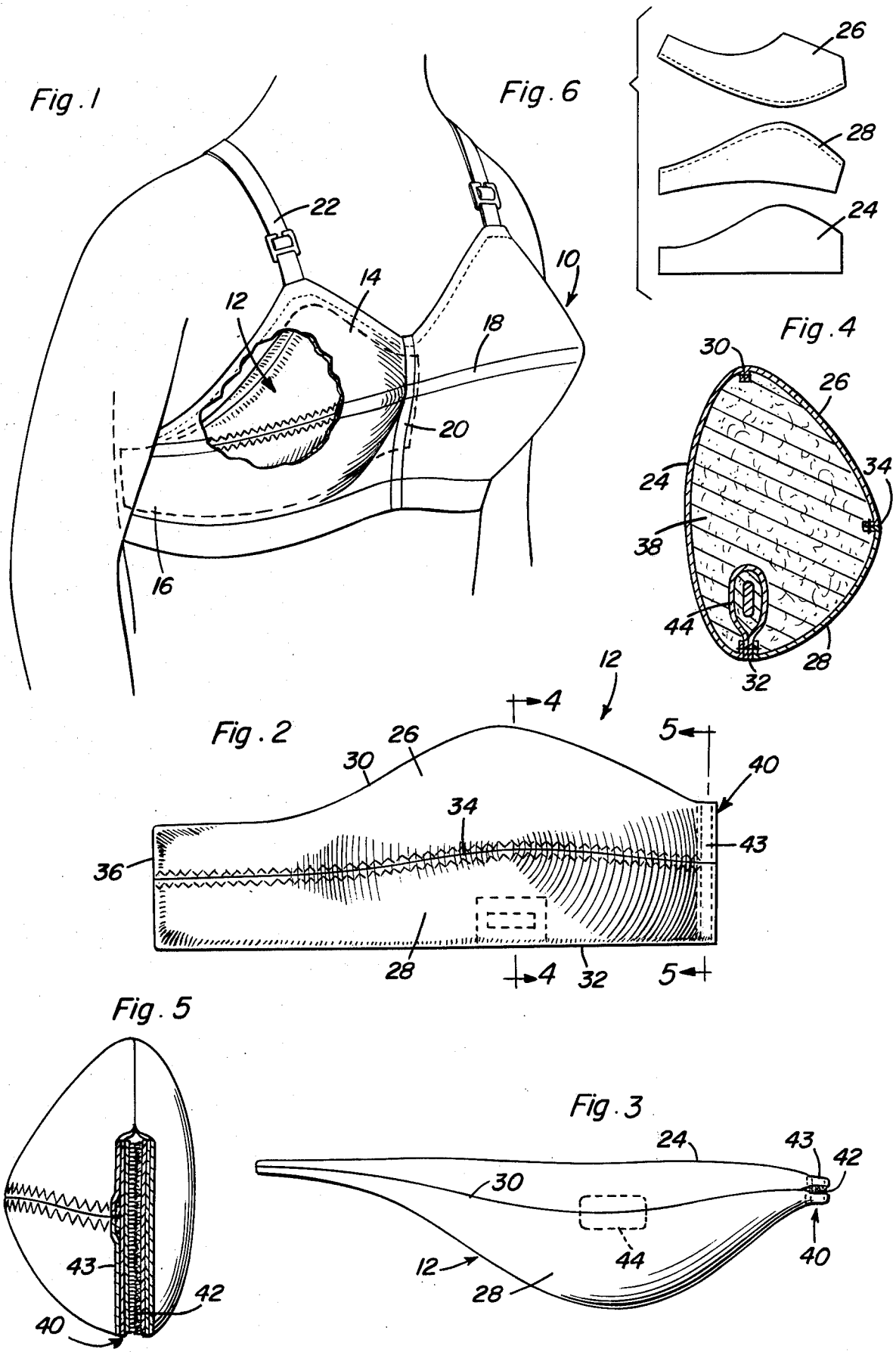

CONTOUR BUSTETTE

This invention relates to a prosthesis adapted to be fitted within a conventional brassiere in order to simulate a natural breast which has been surgically removed.

The use of prostheses by women who have undergone mastectomies, is well known. Breast contour forming prostheses worn under a brassiere are disclosed for example in U.S. Pat. Nos. 814,181, 2,482,297, 3,516,414, 3,641,592 and 3,878,568. Generally, such prostheses include flexible panels that enclose a filler inserted within the cup portion of a brassiere. Such prior breast prostheses are often uncomfortable to the wearer and are somewhat less than perfect in simulating the natural breast shape. It is therefore an important object of the present invention to provide a breast prosthesis that is more universally adaptable and adjustable for use by women having undergone breast surgery including radical mastectomies and wherein the prosthesis is more comfortable to the wearer and more perfectly simulates the natural bust contours.

In accordance with the present invention, the breast prosthesis is formed from three panels consisting of a single rear panel contacting the body of the wearer and two front panels interconnected with the rear panel. The front panels are also interconnected to each other along a horizontal seam aligned with the horizontal seam of a conventional brassiere under which it is inserted. The prosthesis extends from the centerline of the brassiere into the cup portion and to the underarm section. A releasable closure at one end of the prosthesis is aligned with the centerline of the brassiere and retains a filler material between the panels in order to maintain the proper convex curvatures. A weight packet is embedded within the filler and anchored to the lower seam between the rear and front panels. The flexible panels are made of a wash and wear cotton blend material while the filler is made of a polyester fiber. The seams interconnecting the panels may be either sewn on a machine or molded.

These together with other objects and advantages which will become subsequently apparent reside in the details of construction and operation as more fully hereinafter described and claimed, reference being had to the accompanying drawings forming a part hereof, wherein like numerals refer to like parts throughout.

FIG. 1 is a front perspective view showing the prosthesis being worn beneath a conventional brassiere.

FIG. 2 is a front elevational view of the prosthesis itself.

FIG. 3 is a top plan view of the prosthesis shown in FIG. 2.

FIG. 4 is a transverse sectional view taken substantially through a plane indicated by section line 4—4 in FIG. 2.

FIG. 5 is a transverse sectional view taken substantially through a plane indicated by section line 5—5 in FIG. 2.

FIG. 6 illustrates the flexible panels from which the prosthesis is made in accordance with the present invention.

Referring now to te drawings in detail, FIG. 1 illustrates a conventional brassiere 10 being worn by a wearer who has undergone a radical mastectomy and is accordingly fitted with a prosthesis generally referred to by reference numeral 12 simulating one of the wearer's breasts which has been surgically removed. The prosthesis 12 as shown is fitted within the cup and underarm portions 14 and 16 of the brassiere. As in the case of most conventional brassieres, the brassiere 10 includes a horizontal seam 18 that extends between the underarm portions 16 across the centerline seam 20. Shoulder straps 22 are interconnected with the cup portions 14 of the brassiere on either side of the centerline seam 20.

The prosthesis 12 as shown in FIGS. 2, 3 and 4 is formed by a rear, body contacting panel 24 interconnected with a pair of front panels 26 and 28. The panels are made of a suitable flexible material preferably a wash and wear cotton blend such as Dacron and cotton. Further, the rear panel 24 contacting the body of the wearer, is of a single piece forming a smooth convex curvature so as to avoid any discomfort to the wearer. The rear panel 24 is interconnected with the front panels along upper and lower longitudinal seams 30 and 32. The front panels 26 and 28 are interconnected with each other along a horizontal seam 34. In order to conform to the cup and underarm portions of the brassiere, the upper longitudinal edge seam 30 curves upwardly to form an upper cup portion and then converges toward the straight lower edge seam 32 into substantial parallel relationship thereto along an underarm section as more clearly seen in FIG. 2. The flexible panels are all permanently interconnected at the end 36 to enclose a cavity filled with a filler materials 38 as shown in FIG. 4. The filler material thus maintains the convex curvatures of the surfaces formed by the panels. The filler may be made of a suitable washable material such as polyester fiber. The seams 30, 32 and 34 on the other hand may be sewn with a polyester thread and turned in as shown. Alternatively, the seam may be formed by molding the flexible panels to each other.

The three flexible panels from which the prosthesis is formed, are shown in FIG. 6 prior to assembly. The panels are stitched or molded to each other along the seams aforementioned in order to form a cavity into which an adjustably metered amount of filler is inserted through an opening formed at the end oppsite the end 36. The opening into which the filer is introduced is closed by a releasable closure generally referred to be reference numeral 40. As more clearly seen in FIG. 5, the closure 40 is formed by Velcro strips 42 secured to the end strip portions 43 of the closure, these end strip portions being aligned with the centerline seam 20 of the brassiere when the prosthesis is inserted therein.

Dependent upon the size and shape of the natural breast, the prosthesis is weighted by embedding within the filer 38, a weight packet generally referred to by reference numeral 44. The weight packet is formed from a coated lead weight completely wrapped in a fiber-fill and is anchored to the lower longitudinal edge seam 32.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination with a brassiere, a breast prosthesis adapted to be positioned on the body of a mastectomy patient inside one of te cups and underarm side portions of the brassiere that has a seam extending between the side portions across the centerline between the cup portions to which shoulder straps are connected; said prosthesis comprising a single flexible body-contacting panel forming a continuous surface of convex curvature, at least two flexible brassiere-contacting panels peripherally secured to the body-contacting panel and interconnected to each other along a continuous edge portion substantially aligned throughout with the seam of the brassiere, said brassiere-contacting panels forming a breast contour surface of convex curvature and an underarm section extending from the centerline in contact with substantially the entire cup and underarm side portion of the brassiere, closure means releasably connecting the brassiere-contacting panels to the body-contacting panel at an end remote from the underaram section in substantial alignment with said centerline of the brassiere to enclose a cavity, and a mass of filler material retained in said cavity by the closure means to maintain said convex curvatures of the surfaces formed by the panels.

2. The combination of claim 1 wherein brassiere-contacting panels are secured to the body-contacting panel along spaced longitudinal edges extending from the closure means to outline the breast contour surface, one of said edges extending in close adjacency to one of the shoulder straps of the brassiere.

3. The combination of claim 5 including a weighted device embedded in the filler and means anchoring the weighted device to the other of said edges.

4. The combination of claim 1 including a weighted device embedded in the filler below the edge portion.

5. In combination with a brassiere having a pair of cups interconnected at a centerline, underarm side sections connected to the cups and a seam extending between the underarm side sections across the cups, a breast prosthesis adapted to be positioned on the body of a mastectomy patient underneath one of the cups and underarm side sections of the brassiere, comprising two flexible brassiere-contacting panels extending in contact with the one of the cups and underarm side sections of the brassiere, means interconnecting said brassiere-contacting panels along a continuous edge in aligned contact with the seam of the brassiere throughout, a single body-contacting panel peripherally secured to the interconnected brassiere-contacting panels to form a smooth continuous surface including a breast contour portion and an underarm portion, closure means releasably connecting the panels to each other along the centerline to enclose a cavity, and a filler retained in said cavity by the closure means.

* * * * *